US010844416B2

(12) United States Patent
Tescione et al.

(10) Patent No.: US 10,844,416 B2
(45) Date of Patent: Nov. 24, 2020

(54) MANGANESE SUPPLEMENTATION FOR CONTROL OF GLYCOSYLATION IN MAMMALIAN CELL CULTURE PROCESS

(71) Applicant: Biogen MA Inc., Cambridge, MA (US)

(72) Inventors: Lia Tescione, Cambridge, MA (US); Thomas Ryll, Weston, MA (US); Alan Gilbert, Arlington, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 15/578,847

(22) PCT Filed: Jun. 1, 2016

(86) PCT No.: PCT/US2016/035250
§ 371 (c)(1),
(2) Date: Dec. 1, 2017

(87) PCT Pub. No.: WO2016/196621
PCT Pub. Date: Dec. 8, 2016

(65) Prior Publication Data
US 2018/0155753 A1 Jun. 7, 2018

Related U.S. Application Data

(60) Provisional application No. 62/169,488, filed on Jun. 1, 2015.

(51) Int. Cl.
*A61K 38/00* (2006.01)
*C12P 21/00* (2006.01)
*C12N 5/00* (2006.01)
*C07K 16/28* (2006.01)
*C12N 5/073* (2010.01)
*C12N 5/071* (2010.01)

(52) U.S. Cl.
CPC ........ *C12P 21/005* (2013.01); *C07K 16/2842* (2013.01); *C12N 5/0018* (2013.01); *C12N 5/0603* (2013.01); *C12N 5/0682* (2013.01); *C07K 2317/14* (2013.01); *C07K 2317/41* (2013.01); *C12N 2500/20* (2013.01); *C12N 2511/00* (2013.01)

(58) Field of Classification Search
None
See application file for complete search history.

(56) References Cited

U.S. PATENT DOCUMENTS

| 6,077,851 | A * | 6/2000 | Bjork | C07D 215/22 514/312 |
| 8,993,724 | B2 * | 3/2015 | Fischer | C12N 5/0031 530/351 |
| 2003/0064919 | A1 * | 4/2003 | Prayaga | C07K 14/555 424/178.1 |
| 2007/0161084 | A1 | 7/2007 | Crowell et al. | |
| 2008/0081356 | A1 | 4/2008 | Lasko et al. | |
| 2013/0028866 | A1 * | 1/2013 | Gilgun | A61K 38/215 424/85.6 |
| 2016/0166648 | A1 * | 6/2016 | Gilgun | A61P 43/00 424/465 |

OTHER PUBLICATIONS

Hossler et al. (Glycobiology, vol. 19., No. 9, pp. 936-949, 2009).*
Invitation to Pay Additional Fees for Application No. PCT/US2016/035250 dated Sep. 9, 2016.
International Search Report and Written Opinion for Application No. PCT/US2016/035250 dated Oct. 31, 2016.
International Preliminary Report on Patentability for Application No. PCT/US2016/035250 dated Dec. 14, 2017.
Crowell et al., Amino acid and manganese supplementation modulates the glycosylation state of erythropoietin in a CHO culture system. Biotechnology and Bioengineering. Feb. 15, 2007;96(3):538-549.
Grainger et al., CHO cell line specific prediction and control of recombinant monoclonal antibody N-glycosylation. Biotechnology and Bioengineering. Nov. 2013;110(11):2970-2983.
Gramer et al., Modulation of Antibody Galactosylation Through Feeding of Uridine, Manganese Chloride, and Galactose. Biotechnology and Bioengineering. Jul. 2011;108(7):1591-1602.
Tharmalingam et al., A framework for real-time glycosylation monitoring (RT-GM) in mammalian cell culture. Biotechnology and Bioengineering. Jun. 2015;112(6):1146-1154.
Office Action for Application No. EP 16730594.5 dated Jun. 19, 2019.
Damiani et al., Effects of butyrate and manganese on productivity, sialylation, N-glycosylation site occupancy and biological properties of CHO-derived human thyrotropin. Journal of Biotechnology. Sep. 2014;185:S106.

* cited by examiner

*Primary Examiner* — Hope A Robinson
(74) *Attorney, Agent, or Firm* — Wolf, Greenfield & Sacks, P.C.

(57) ABSTRACT

The present invention pertains to a cell culture medium comprising manganese as a media supplement, which was shown to control recombinant protein glycosylation and methods of using thereof. The present invention further pertains to a method of controlling or manipulating glycosylation of a recombinant protein of interest in a large scale cell culture.

Figure 1A:
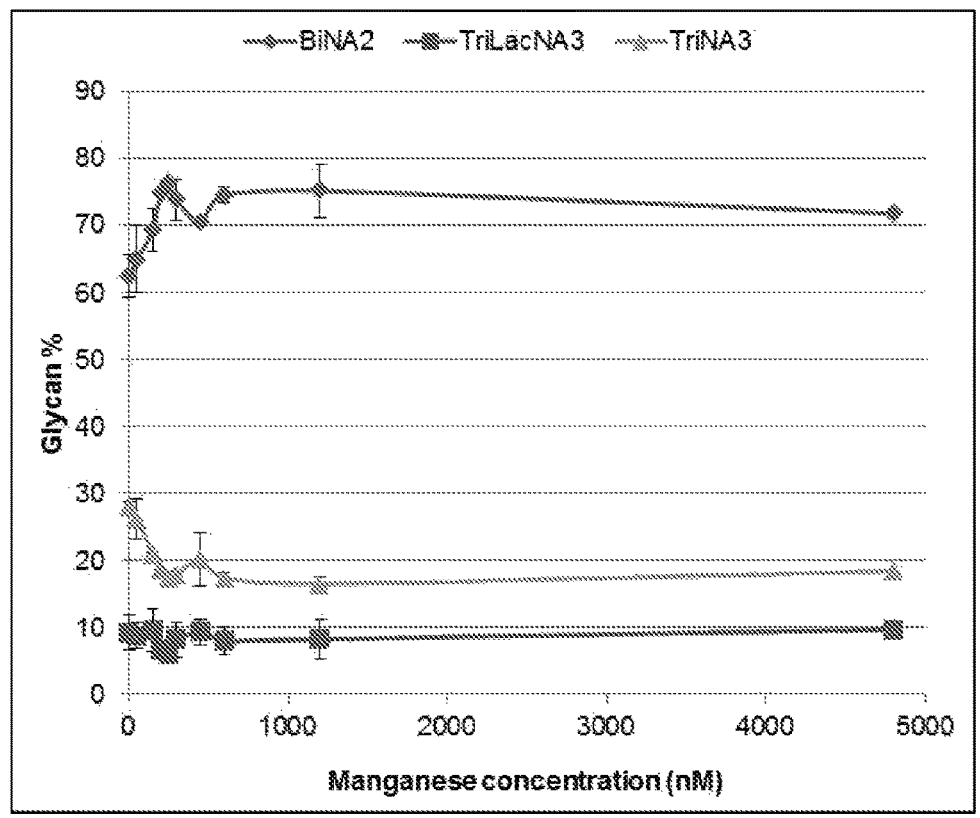

21 Claims, 2 Drawing Sheets
Specification includes a Sequence Listing.

SEQUENCE LISTING

```
<160> NUMBER OF SEQ ID NOS: 1

<210> SEQ ID NO 1
<211> LENGTH: 166
<212> TYPE: PRT
<213> ORGANISM: Artificial Sequence
<220> FEATURE:
<223> OTHER INFORMATION: Synthetic polypeptide

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

MANGANESE SUPPLEMENTATION FOR CONTROL OF GLYCOSYLATION IN MAMMALIAN CELL CULTURE PROCESS

RELATED APPLICATIONS

This application is a national stage filing under 35 U.S.C. § 371 of PCT International Application No. PCT/US2016/035250, filed Jun. 1, 2016 entitled "MANGANESE SUPPLEMENTATION FOR CONTROL OF GLYCOSYLATION IN MAMMALIAN CELL CULTURE PROCESS" which claims the benefit under 35 U.S.C. § 119(e) of U.S. provisional patent application Ser. No. 62/169,488, filed Jun. 1, 2015, each of which is incorporated by reference herein in its entirety.

BACKGROUND OF THE INVENTION

Field of the Invention

The present invention pertains to a cell culture medium comprising manganese as a media supplement that was shown to control recombinant protein antennarity and/or glycosylation and methods of using thereof. The present invention further pertains to a method of controlling or manipulating antennarity and/or glycosylation of a recombinant protein of interest in a large scale cell culture, comprising controlling or manipulating the concentration of manganese in the cell culture medium.

Background Art

Over the last few decades, much research has focused on the production of therapeutic recombinant proteins, e.g., monoclonal antibodies. While media containing sera or hydrolysates has been utilized, chemically defined media were also developed in order to eliminate the problematic lot-to-lot variation of complex components (Luo and Chen, *Biotechnology and Bioengineering* 97(6):1654-1659 (2007)). An improved understanding of cell culture has permitted a shift to chemically defined medium without compromising growth, viability, titer, etc. To date optimized chemically defined processes have been reported with titers as high as 7.5-10 g/L (Huang et al., *Biotechnology Progress* 26(5):1400-1410 (2010); Ma et al., *Biotechnology Progress* 25(5):1353-1363 (2009); Yu et al., *Biotechnology and Bioengineering* 108(5):1078-1088 (2011)). In general, the high titer chemically defined processes are fed batch processes with cultivation times of 11-18 days. The process intensification has been achieved without compromising product quality while maintaining relatively high viabilities.

Achievement of a robust, scalable production process includes more than increasing the product titer while maintaining high product quality. The process must also predictably require the main carbohydrate source remain constant, such that the feeding strategy does not need to change across scales. As many processes use glucose as the main carbohydrate, and have lactate and ammonium as the main byproducts, the time course of these three critical chemicals should also scale.

A number of reports have demonstrated mammalian host cell-specific processing of N-glycans associated with recombinant proteins (James et al., *Bio/Technology*, 13:592-596 (1995); Lifely et al., *Glycobiology,* 5:813-822 (1995)). These differences may be important for therapeutic proteins as they can directly alter the antigenicity, rate of clearance in vivo, and stability of recombinant proteins (Jenkins et al., *Nature Biotechnol.* 14:975-981 (1996)). Thus, it is important not only to be able to characterize glycans bound to a therapeutic recombinant protein to predict the consequences for in vivo safety and efficacy, but also to understand the cellular controls underpinning glycan processing in a potential host cell enabling the implementation of appropriate strategies to control cellular glycosylation (Grabenhosrt et al., *Glycoconjug. J.,* 16:81-97 (1999); James and Baker, Encyclopedia of bioprocess technology: Fermentation, biocatalysis and bioseparation. New York: John Wiley & Sons. p. 1336-1349 (1999)).

Thus, there is a need in the art for identification of methods that can predictably control glycosylation of proteins of interest.

BRIEF SUMMARY OF THE INVENTION

In one aspect, the present invention is directed to a method for achieving a predetermined glycosylation profile of an anti-α4-integrin antibody comprising providing manganese to a cell culture at a concentration that falls within a target manganese concentration range, wherein the cell culture comprises host cells producing the anti-α4-integrin antibody.

In another aspect, the invention is directed to supplementing the cell culture with manganese if the manganese concentration in the cell culture is below the target manganese concentration range.

In another aspect, the invention is directed to a method for achieving a predetermined glycosylation profile of an anti-α4-integrin antibody comprising (i) determining a manganese concentration in a component of a cell culture medium, (ii) if the manganese concentration is below a target manganese concentration range, supplementing the cell culture medium with the component to achieve a manganese concentration within the target manganese concentration range, and (iii) culturing a recombinant host cell producing an anti-α4-integrin antibody in the cell culture medium comprising the cell culture medium component.

In another aspect, the invention is directed to a method for achieving a predetermined glycosylation profile of an anti-α4-integrin antibody comprising (i) determining a manganese concentration in a component of a cell culture medium, (ii) if the manganese concentration is below a target manganese concentration range, adding manganese to the component of the cell culture medium to achieve a manganese concentration within the target manganese concentration range, (iii) producing a cell culture medium using the component of cell culture medium with the target manganese concentration, and (iv) culturing a recombinant host cell producing an anti-α4-integrin antibody in the cell culture medium comprising the cell culture medium component with the target manganese concentration.

In another aspect, the invention is directed to a method for optimizing a cell culture medium for the production of an anti-α4-integrin antibody comprising (i) determining the amount of manganese in a cell culture medium or a component used to produce a cell culture medium, and (ii) if the amount of manganese is below a target range, supplementing the cell culture medium or the component of the cell culture medium with manganese to achieve an amount of manganese within the target range, wherein the target range is sufficient to produce anti-α4-integrin antibody with a predetermined glycosylation profile.

In another aspect, the invention is directed to a method for optimizing a cell culture medium for the production of an anti-α4-integrin antibody comprising (i) determining the amount of manganese in a cell culture medium or a component used to produce a cell culture medium, and (ii) if the amount of manganese is above a target range, removing manganese from the cell culture medium or the component of the cell culture medium to achieve an amount of manganese within the target range, wherein the target range is sufficient to produce anti-α4-integrin antibody with a predetermined glycosylation profile.

In one embodiment, the predetermined glycosylation profile of the anti-α4-integrin antibody comprises 13 to 32% galactosylation. In a further embodiment, the predetermined glycosylation profile of the anti-α4-integrin antibody comprises 18 to 31% galactosylation. In a further embodiment, the predetermined glycosylation profile of the anti-α4-integrin antibody comprises about 24% galactosylation.

In one embodiment, the predetermined glycosylation profile of the anti-α4-integrin antibody comprises 0.7 to 3.6% sialylation. In a further embodiment, the predetermined glycosylation profile of the anti-α4-integrin antibody comprises 1.0 to 2.2% sialylation. In a further embodiment, the predetermined glycosylation profile of the anti-α4-integrin antibody comprises about 1.6% sialylation.

In one embodiment, the target manganese concentration range in the cell culture for anti-α4-integrin antibody is 0.025 µM to 10 µM. In another embodiment, the target manganese concentration range in the cell culture for anti-α4-integrin antibody is 0.1 µM to 2.5 µM. In another embodiment, the target manganese concentration range in the cell culture for anti-α4-integrin antibody is 0.2 µM to 2 µM.

In one embodiment, the target manganese concentration range in the cell culture for anti-α4-integrin antibody is at day 0 between 0.002 µM and 0.4 µM and at day 13 between 0.04 µM and 1 µM.

In one aspect, the present invention is directed to a method for achieving a predetermined glycosylation profile of an interferon beta-1a polypeptide comprising providing manganese to a cell culture at a concentration that falls within a target manganese concentration range, wherein the cell culture comprises host cells producing the interferon beta-1a polypeptide. In another aspect, the invention is directed to supplementing the cell culture with manganese if the manganese concentration in the cell culture is below the target manganese concentration range.

In another aspect, the invention is directed to a method for achieving a predetermined glycosylation profile of an interferon beta-1a polypeptide comprising (i) determining a manganese concentration in a component of a cell culture medium, (ii) if the manganese concentration is below a target manganese concentration range, supplementing the cell culture medium with the component to achieve a manganese concentration within the target manganese concentration range, and (iii) culturing a recombinant host cell producing an interferon beta-1a polypeptide in the cell culture medium comprising the cell culture medium component.

In another aspect, the invention is directed to a method for achieving a predetermined glycosylation profile of an interferon beta-1a polypeptide comprising (i) determining a manganese concentration in a component of a cell culture medium, (ii) if the manganese concentration is below a target manganese concentration range, adding manganese to the component of the cell culture medium to achieve a manganese concentration within the target manganese concentration range, (iii) producing a cell culture medium using the component of cell culture medium with the target manganese concentration, and (iv) culturing a recombinant host cell producing an interferon beta-1a polypeptide in the cell culture medium comprising the cell culture medium component with the target manganese concentration.

In another aspect, the invention is directed to a method for optimizing a cell culture medium for the production of an interferon beta-1a polypeptide comprising (i) determining the amount of manganese in a cell culture medium or a component used to produce a cell culture medium, and (ii) if the amount of manganese is below a target range, supplementing the cell culture medium or the component of the cell culture medium with manganese to achieve an amount of manganese within the target range, wherein the target range is sufficient to produce interferon beta-1a polypeptide with a predetermined glycosylation profile.

In another aspect, the invention is directed to a method for optimizing a cell culture medium for the production of an interferon beta-1a polypeptide comprising (i) determining the amount of manganese in a cell culture medium or a component used to produce a cell culture medium, and (ii) if the amount of manganese is above a target range, removing manganese from the cell culture medium or the component of the cell culture medium to achieve an amount of manganese within the target range, wherein the target range is sufficient to produce interferon beta-1a polypeptide with a predetermined glycosylation profile.

In one embodiment, the predetermined glycosylation profile of the interferon beta-1a polypeptide comprises 91 to 100% sialylation. In a further embodiment, the predetermined glycosylation profile of the interferon beta-1a polypeptide comprises 91 to 97% sialylation. In a further embodiment, the predetermined glycosylation profile of the interferon beta-1a polypeptide comprises 95% sialylation.

In one embodiment, the predetermined glycosylation profile of the interferon beta-1a polypeptide comprises 55 to 85% biantennary glycoproteins. In a further embodiment, the predetermined glycosylation profile of the interferon beta-1a polypeptide comprises 66 to 73% biantennary glycoproteins. In a further embodiment, the predetermined glycosylation profile of the interferon beta-1a polypeptide comprises 70% biantennary glycoproteins.

In one embodiment, the predetermined glycosylation profile of the interferon beta-1a polypeptide comprises 12 to 46% triantennary glycoproteins. In a further embodiment, the predetermined glycosylation profile of the interferon beta-1a polypeptide comprises 26 to 35% triantennary glycoproteins. In a further embodiment, the predetermined glycosylation profile of the interferon beta-1a polypeptide comprises 30% triantennary glycoproteins.

In one embodiment, the predetermined glycosylation profile of the interferon beta-1a polypeptide comprises a biantennary glycoprotein to triantennary glycoprotein ratio of about 1.8 to 4.6. In a further embodiment, the predetermined glycosylation profile of the interferon beta-1a polypeptide comprises a biantennary glycoprotein to triantennary glycoprotein ratio of about 2.0 to 2.5. In a further embodiment, the predetermined glycosylation profile of the interferon beta-1a polypeptide comprises a biantennary glycoprotein to triantennary glycoprotein ratio of about 2.3.

In one embodiment, the target manganese concentration range in the cell culture for interferon beta-1a polypeptide is 0.1 µM to 5 µM. In another embodiment, the target manganese concentration range in the cell culture for interferon beta-1a polypeptide is 0.2 µM to 4.8 µM. In another embodiment, the target manganese concentration range in the cell culture for interferon beta-1a polypeptide 0.3 µM to 4.8 µM.

In one embodiment, the target manganese concentration in the cell culture for anti-α4-integrin antibody or interferon beta-1a polypeptide is maintained through a feedback loop. In another embodiment, the manganese concentration is constantly monitored and maintained within the target manganese concentration range. In another embodiment, the target manganese concentration is achieved with a single dose of manganese.

In one aspect, the present invention is directed to a method for achieving a predetermined glycosylation profile of a rFVIIIFc polypeptide comprising providing manganese to a cell culture at a concentration that falls within a target manganese concentration range, wherein the cell culture comprises host cells producing the a rFVIIIFc polypeptide. In another aspect, the invention is directed to supplementing the cell culture with manganese if the manganese concentration in the cell culture is below the target manganese concentration range.

In another aspect, the invention is directed to a method for achieving a predetermined glycosylation profile of a rFVIIIFc polypeptide comprising (i) determining a manganese concentration in a component of a cell culture medium, (ii) if the manganese concentration is below a target manganese concentration range, supplementing the cell culture medium with the component to achieve a manganese concentration within the target manganese concentration range, and (iii) culturing a recombinant host cell producing an a rFVIIIFc polypeptide in the cell culture medium comprising the cell culture medium component.

In another aspect, the invention is directed to a method for achieving a predetermined glycosylation profile of a rFVIIIFc polypeptide comprising (i) determining a manganese concentration in a component of a cell culture medium, (ii) if the manganese concentration is below a target manganese concentration range, adding manganese to the component of the cell culture medium to achieve a manganese concentration within the target manganese concentration range, (iii) producing a cell culture medium using the component of cell culture medium with the target manganese concentration, and (iv) culturing a recombinant host cell producing a rFVIIIFc polypeptide in the cell culture medium comprising the cell culture medium component with the target manganese concentration.

In another aspect, the invention is directed to a method for optimizing a cell culture medium for the production of a rFVIIIFc polypeptide comprising (i) determining the amount of manganese in a cell culture medium or a component used to produce a cell culture medium, and (ii) if the amount of manganese is below a target range, supplementing the cell culture medium or the component of the cell culture medium with manganese to achieve an amount of manganese within the target range, wherein the target range is sufficient to produce a rFVIIIFc polypeptide with a predetermined glycosylation profile.

In another aspect, the invention is directed to a method for optimizing a cell culture medium for the production of a rFVIIIFc polypeptide comprising (i) determining the amount of manganese in a cell culture medium or a component used to produce a cell culture medium, and (ii) if the amount of manganese is above a target range, removing manganese from the cell culture medium or the component of the cell culture medium to achieve an amount of manganese within the target range, wherein the target range is sufficient to produce a rFVIIIFc polypeptide with a predetermined glycosylation profile.

In one embodiment, the predetermined glycosylation profile of the rFVIIIFc comprises 15 to 32% G0+Man6. In a further embodiment, the predetermined glycosylation profile of the rFVIIIFc comprises 16 to 29% G0+Man6. In a further embodiment, the predetermined glycosylation profile of the rFVIIIFc comprises 17 to 27% G0+Man6.

In one embodiment, the predetermined glycosylation profile of the rFVIIIFc comprises 19 to 30% G1+Man7. In a further embodiment, the predetermined glycosylation profile of the rFVIIIFc comprises 22 to 27% G1+Man7. In a further embodiment, the predetermined glycosylation profile of the rFVIIIFc comprises 24 to 26% G1+Man7.

In one embodiment, the predetermined glycosylation profile of the rFVIIIFc comprises 6 to 17% G2+Man9. In a further embodiment, the predetermined glycosylation profile of the rFVIIIFc comprises 7 to 16% G2+Man9. In a further embodiment, the predetermined glycosylation profile of the rFVIIIFc comprises 10 to 15% G2+Man9.

In one embodiment, the target manganese concentration range in the cell culture for a rFVIIIFc polypeptide is 30 nM to 1800 nM. In another embodiment, the target manganese concentration range in the cell culture for a rFVIIIFc polypeptide is 50 nM to 300 nM. In another embodiment, the target manganese concentration range in the cell culture for a rFVIIIFc polypeptide is 75 nM to 200 nM.

In one embodiment, the target manganese concentration in the cell culture for anti-$\alpha$4-integrin antibody, or interferon beta-1a polypeptide, or a rFVIIIFc polypeptide is maintained through a feedback loop. In another embodiment, the manganese concentration is constantly monitored and maintained within the target manganese concentration range. In another embodiment, the target manganese concentration is achieved with a single dose of manganese.

In one embodiment, the anti-$\alpha$4-integrin antibody, interferon beta-1a polypeptide, or rFVIIIFc polypeptide is produced by a eukaryotic host cell. In a preferred embodiment, the eukaryotic host cell is a mammalian host cell.

In one embodiment, the anti-$\alpha$4-integrin antibody, interferon beta-1a polypeptide, or rFVIIIFc polypeptide is produced at a manufacturing scale. In another embodiment, the manganese concentration alters the levels of the isoform variants of the anti-$\alpha$4-integrin antibody, interferon beta-1a polypeptide, or rFVIIIFc polypeptide.

In one embodiment, the anti-$\alpha$4-integrin antibody is natalizumab. In one embodiment, the interferon beta-1a polypeptide is AVONEX® with SEQ ID NO:1

BRIEF DESCRIPTION OF THE DRAWINGS/FIGURES

Figure 1B:
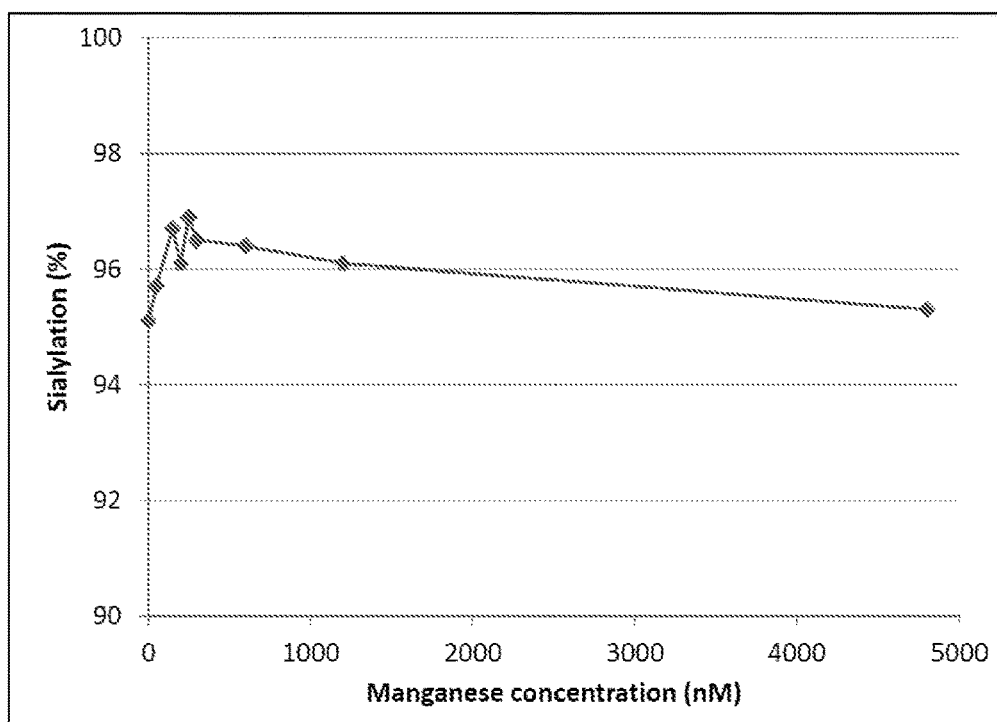

FIG. 1A and FIG. 1B show the effect of manganese concentration on percent glycosylation of a recombinant interferon beta-1a polypeptide. The X-axis shows manganese concentration of cell culture media. The Y-axis shows the percentage of glycans in recombinant interferon beta-1a polypeptide. Specifically, the percent biantennary, percent TriLac, and the percent triantennary glycosylation of the recombinant interferon beta-1a polypeptide are shown in FIG. 1A and percentage sialylation is shown in FIG. 1B.

Figure 2:
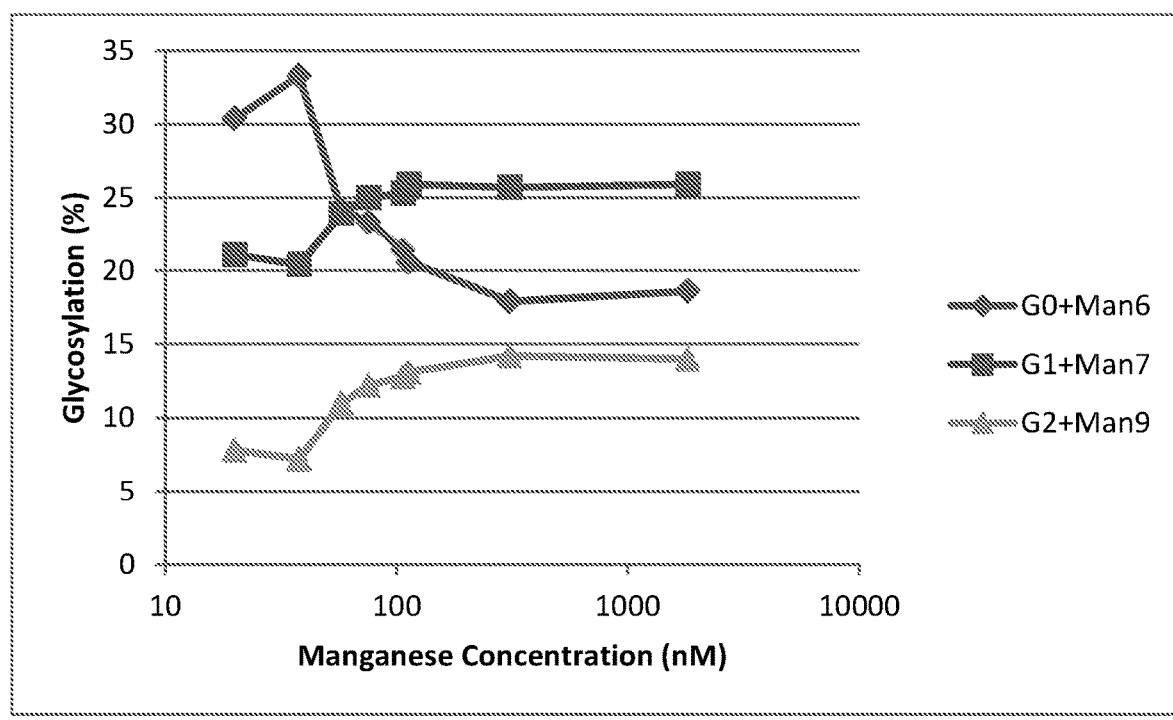

FIG. 2 shows the effect of manganese concentration on percent glycosylation of recombinant Factor VIII (rFVIIIFc). The X-axis shows manganese concentration of cell culture media. The Y-axis shows the percentage of glycosylation of a rFVIIIFc. Specifically, percent terminal mannose-6 with a G0 modification (G0+Man6), percent terminal mannose-7 with a G1 modification (G1+Man7), and percent terminal mannose-9 with a G2 modification (G2+Man9) is shown.

DETAILED DESCRIPTION OF THE INVENTION

The present invention is based on the recognition that cell culture media supplemented with manganese provides the ability to control and manipulate the glycolsylation patterns of recombinant glycoproteins produced in eukaryotic cell cultures. Such glyclosylation patterns include, without limitation, the antennarity and level of galactosylation.

The present invention is also applicable to modifying the glycosylation of a recombinant glycoprotein of interest such that it falls within the quality attribute ranges for the desired product. For example, the present invention is applicable to modifying the glycosylation profile of a recombinant glycoprotein of interest to more closely resemble, match, or substantially match the glycosylation pattern of a reference sample of the same glycoprotein. Differences between various manufacturing processes can result in glycoproteins with identical amino acid sequences having different glycosylation patterns depending on, for example, conditions for growth, cell line used to express the glycoprotein, etc.

Provided herein are methods for achieving a predetermined glycosylation profile of a recombinant glycoprotein of interest comprising adjusting the concentration of manganese in a cell culture to achieve a target concentration range, wherein the cell culture comprises host cells producing the recombinant glycoprotein of interest. Also provided herein are methods for optimizing a cell culture medium for the production of a recombinant glycoprotein of interest comprising (i) determining the amount of manganese in a cell culture medium or a component used to produce a cell culture medium, and (ii) adjusting the concentration of manganese in the cell culture medium to achieve an amount of manganese within the target range, wherein the target range is sufficient to produce the recombinant glycoprotein of interest with a predetermined galactosylation profile.

For example, provided herein are methods for achieving a predetermined glycosylation profile of an anti-α4-integrin antibody, an interferon beta-1a polypeptide, or a rFVIIIFc polypeptide comprising providing manganese to a cell culture at a concentration that falls within a target manganese concentration range, wherein the cell culture comprises host cells producing the anti-α4-integrin antibody, an interferon beta-1a polypeptide, or a rFVIIIFc polypeptide.

Also provide herein are methods for achieving a predetermined glycosylation profile of an anti-α4-integrin antibody, an interferon beta-1a polypeptide, or a rFVIIIFc polypeptide comprising (i) determining a manganese concentration in a component of a cell culture medium, (ii) if the manganese concentration is below a target manganese concentration range, supplementing the cell culture medium with the component to achieve a manganese concentration within the target manganese concentration range, and (iii) culturing a recombinant host cell producing an anti-α4-integrin antibody, an interferon beta-1a polypeptide, or a rFVIIIFc polypeptide in the cell culture medium comprising the cell culture medium component.

Also provided herein are methods for achieving a predetermined glycosylation profile of an anti-α4-integrin antibody, an interferon beta-1a polypeptide, or a rFVIIIFc polypeptide comprising (i) determining a manganese concentration in a component of a cell culture medium, (ii) if the manganese concentration is below a target manganese concentration range, adding manganese to the component of the cell culture medium to achieve a manganese concentration within the target manganese concentration range, (iii) producing a cell culture medium using the component of cell culture medium with the target manganese concentration, and (iv) culturing a recombinant host cell producing an anti-α4-integrin antibody, an interferon beta-1a polypeptide, or a rFVIIIFc polypeptide in the cell culture medium comprising the cell culture medium component with the target manganese concentration.

Also provided herein are methods for optimizing a cell culture medium for the production of an anti-α4-integrin antibody, an interferon beta-1a polypeptide, or a rFVIIIFc polypeptide comprising (i) determining the amount of manganese in a cell culture medium or a component used to produce a cell culture medium, and (ii) if the amount of manganese is above a target range, removing manganese from the cell culture medium or the component of the cell culture medium to achieve an amount of manganese within the target range, wherein the target range is sufficient to produce anti-α4-integrin antibody, an interferon beta-1a polypeptide, or a rFVIIIFc polypeptide with a predetermined glycosylation profile.

I. Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various embodiments of the disclosure, which can be had by reference to the specification as a whole. Accordingly, the terms defined immediately below are more fully defined by reference to the specification in its entirety.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

The term "glycoprotein" refers to a polypeptide or protein coupled to at least one carbohydrate moiety, e.g., a polysaccharide or an oligosaccharide, that is attached to the protein via an oxygen-containing or a nitrogen-containing side chain of an amino acid residue, e.g., a serine or threonine residue ("O-linked") or an asparagine residue ("N-linked"). The term "glycan" refers to a polysaccharide or an oligosaccharide, e.g., a polymer comprised of monosaccharides. Glycans can be homo- or heteropolymers of monosaccharide residues, and can be linear or branched.

As used herein, the "glycosylation pattern" of a recombinant glycoprotein of interest refers to various physical characteristics of the glycoprotein's polysaccharides or oligosaccharides, such as, e.g., the quantity and quality of various monosaccharides present, the degree of branching, and/or the attachment (e.g., N-linked or O-linked). The "glycosylation pattern" of a glycoprotein can also refer to the functional characteristics imparted by the glycoprotein's oligosaccharides and polysaccharides. For example, the extent to which the glycoprotein can bind to FcγRIIIa and induce antibody-dependent cellular cytotoxicity (ADCC).

"Fucosylation" refers to the degree and distribution of fucose residues on polysaccharides and oligosaccharides, for example, N-glycans, 0-glycans and glycolipids. Therapeutic glycoproteins, e.g., antibodies or Fc fusion proteins, with non-fucosylated, or "afucosylated" N-glycans exhibit dramatically enhanced antibody-dependent cellular cytotoxicity (ADCC) due to the enhancement of FcγRIIIa binding capacity without any detectable change in complement-dependent cytotoxicity (CDC) or antigen binding capability. In certain situations, e.g., cancer treatment, non-fucosylated or "afucosylated" antibodies are desirable because they can achieve therapeutic efficacy at low doses, while inducing high cellular cytotoxicity against tumor cells, and triggering high effector function in NK cells via enhanced interaction with FcγRIIIa. In other situations, e.g., treatment of inflammatory or autoimmune diseases, enhanced ADCC and FcγRIIIa binding is not desirable, and accordingly therapeutic glycoproteins with higher levels of fucose residues in their N-glycans can be preferable. As used herein, the term "% afucose" refers to the percentage of non-fucosylated N-glycans present on a recombinant glycoprotein of interest. A higher % afucose denotes a higher number of non-fucosylated N-glycans, and a lower % afucose denotes a higher number of fucosylated N-glycans.

"Sialylation" refers to the type and distribution of sialic acid residues on polysaccharides and oligosaccharides, for example, N-glycans, O-glycans and glycolipids. Sialic acids are most often found at the terminal position of glycans. Sialylation can significantly influence the safety and efficacy profiles of these proteins. In particular, the in vivo half-life of some biopharmaceuticals correlates with the degree of oligosaccharide sialylation. Furthermore, the sialylation pattern can be a very useful measure of product consistency during manufacturing.

The two main types of sialyl residues found in biopharmaceuticals produced in mammalian expression systems are N-acetyl-neuraminic acid (NANA) and N-glycolyl-neuraminic acid (NGNA). These usually occur as terminal structures attached to galactose (Gal) residues at the non-reducing terminii of both N- and O-linked glycans.

"Galactosylation" refers to the type and distribution of galactose residues on polysaccharides and oligosaccharides. Galactose refers to a group of monosaccharides which include open chain and cyclic forms. An important disaccharide form of galactose is galactose-alpha-1,3-galactose (α-gal).

"Antennarity" refers to the ratio of biantennary to triantennary of polysaccharides and oligosacchrides. The glycans in glycoproteins may differ by the number of branches making up the glycans, leading to biantennary and triantennary structures.

The term "undesirable side effects" refers to certain aspects and results of glycosylation which, under certain circumstances, are to be minimized or avoided. In certain aspects, a side effect to be reduced or avoided is a substantial increase in the level of α-gal. In another aspect a side effect to be reduced or avoided is a substantial reduction in sialic acid levels. In various aspects the methods described herein achieve certain glycosylation patterns without substantially affecting culture density, cell viability level, or both. In certain aspects, a "side effect" which might be undesirable in one glycoprotein, e.g., a decrease in fucose levels (increases ADCC and FcγRIIIa binding) in an antibody used to treat an inflammatory disease, might be desirable in another glycoprotein, e.g., in an antibody used to treat cancer.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

"Recombinantly expressed glycoprotein" and "recombinant glycoprotein" as used herein refer to a glycoprotein expressed from a host cell that has been genetically engineered to express that glycoprotein. The recombinantly expressed glycoprotein can be identical or similar to glycoproteins that are normally expressed in the mammalian host cell. The recombinantly expressed glycoprotein can also be foreign to the host cell, i.e. heterologous to peptides normally expressed in the mammalian host cell. Alternatively, the recombinantly expressed glycoprotein can be chimeric in that portions of the glycoprotein contain amino acid sequences that are identical or similar to glycoproteins normally expressed in the mammalian host cell, while other portions are foreign to the host cell. In certain embodiments, the recombinant glycoprotein comprises an antibody or fragments thereof. As used herein, the terms "recombinantly expressed glycoprotein" and "recombinant glycoprotein" also encompasses an antibody produced by a hybridoma.

The term "chimeric," polypeptide or antibody as used herein, means a polypeptide or antibody that includes within it amino acid sequences (or portions thereof such as subsequences or peptides) from at least two different sources, such as mouse and human. Chimeric polypeptides can include one or more linkers joining its portions. Chimeric polypeptides or antibodies can include additional peptides such as signal sequences and sequences such as 6His and FLAG that aid in protein purification or detection.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization, Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein, Sambrook et al., Molecular Cloning: A Laboratory Manual, pp. 18.1-18.88 (Cold Spring Harbor Laboratory Press, 1989).

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of a molecule of interest may be assessed in vivo, e.g., in an animal model such as that disclosed in Clynes et al. PNAS (USA) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The term "basal media formulation" or "basal media" as used herein refers to any cell culture media used to culture cells that has not been modified either by supplementation, or by selective removal of a certain component.

The term "component" refers to an ingredient or a part of an additive or cell culture medium.

As used herein, the terms "additive" or "supplement" refer to any supplementation made to a basal medium to achieve the goals described in this disclosure. An "additive" or "supplement" can include a single substance, e.g., manganese chloride, or can include multiple substances, e.g., various manganese salts. The terms "additive" or "supplement" refer to the all of the components added, even though they need not be added at the same time, and they need not be added in the same way. For example, one or more components of an "additive" or "supplement" can be added as a single bolus or two or more boli from a stock solution, while other components of the same "additive" or "supplement" can be added as part of a feed medium. In addition, any one or more components of an "additive" or "supplement" can be present in the basal medium from the beginning of the cell culture.

The terms "culture", "cell culture" and "eukaryotic cell culture" as used herein refer to a eukaryotic cell population, either surface-attached or in suspension that is maintained or grown in a medium (see definition of "medium" below) under conditions suitable to survival and/or growth of the cell population. As will be clear to those of ordinary skill in the art, these terms as used herein can refer to the combination comprising the mammalian cell population and the medium in which the population is suspended.

The terms "media", "medium", "cell culture medium", "culture medium", "tissue culture medium", "tissue culture media", and "growth medium" as used herein refer to a solution containing nutrients, which nourish growing cultured eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium"—a serum-free medium that contains no proteins, hydrolysates or components of unknown composition. Defined media are free of animal-derived components and all components have a known chemical structure. One of skill in the art understands a defined medium can comprise recombinant glycoproteins or proteins, for example, but not limited to, hormones, cytokines, interleukins and other signaling molecules.

The cell culture medium is generally "serum free" when the medium is essentially free of serum, or fractions thereof, from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The term "cell density" as used herein refers to that number of cells present in a given volume of medium.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. A fed-batch culture is typically stopped at some point and the cells and/or components in the medium are harvested and optionally purified.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and can be 10, 50, 100, 250, 500, 1000, 2000, 2500, 3000, 5000, 8000, 10,000, 12,0000, 15,000, 20,000, 30,000 liters or more, or any volume in between. For example, a bioreactor will be 10 to 5,000 liters, 10 to 10,000 liters, 10 to 15,000 liters, 10 to 20,000 liters, 10 to 30,000 liters, 50 to 5,000 liters, 50 to 10,000 liters, 50 to 15,000 liters, 50 to 20,000 liters, 50 to 30,000 liters, 1,000 to 5,000 liters, or 1,000 to 3,000 liters. A bioreactor can be a stirred-tank bioreactor or a shake flask. The internal conditions of the bioreactor, for example, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the glycoprotein or protein of interest. The volume of the large-scale cell culture production bioreactor is typically at least 500 liters and can be 1000, 2000, 2500, 5000, 8000, 10,000, 12,0000, 15,000 liters or more, or any volume in between. For example, the large scale cell culture reactor will be between about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a large scale cell culture reactor will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose suitable bioreactors for use in practicing the present invention.

The term "stirred-tank bioreactor" as used herein refers to any vessel used for the growth of a mammalian cell culture that has an impeller.

The term "shake flask" as used herein refers to any vessel used for the growth of a mammalian cell culture that does not have an impeller.

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

The term "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The term "titer" as used herein refers to the total amount of recombinantly expressed glycoprotein or protein produced by a cell culture divided by a given amount of medium volume. Titer is typically expressed in units of milligrams of glycoprotein or protein per milliliter of medium or in units of grams of glycoprotein or protein per liter of medium.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., cellular viability). The difference between said two values is, for example, less than about 50%, less than about 40%, less than about 30%, less than about 20%, and/or less than about 10% as a function of the reference/comparator value.

The phrase "substantially reduced," or "substantially different," as used herein with regard to amounts or numerical values (and not as reference to the chemical process of reduction), denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., cellular viability). The difference between said two values is, for example, greater than about 10%, greater than about 20%, greater than about 30%, greater than about 40%, and/or greater than about 50% as a function of the value for the reference/comparator molecule.

II. Supplementation of Cell Culture Medium to Control Glycosylation Patterns

Provided herein are methods to culture eukaryotic cells engineered to express a recombinant glycoprotein of interest. Specifically this disclosure provides methods for controlling the glycosylation patterns of a recombinant glycoprotein of interest by supplementing a tissue culture medium in which the cells are growing and/or producing the recombinant glycoprotein of interest with an additive, or culturing eukaryotic cells engineered to express a glycoprotein of interest in a tissue culture medium, which has been supplemented with such an additive. In certain embodiments, glycoproteins produced by the methods provided are recovered. The methods are based on the recognition that growth of cells expressing a recombinant glycoprotein of interest in cell culture medium supplemented with manganese can result in alterations to eukaryotic cell glycosylation patterns, such as the level of galactosylation. In certain embodiments, the manganese added is manganese chloride. In certain embodiments, the alteration of the glycosylation pattern of the recombinant glycoprotein of interest comprises a reduced level of galactosylation.

In one embodiment, the recombinant glycoprotein of interest comprises a predetermined galactosylation profile. In one embodiment, the recombinant glycoprotein of interest comprises a predetermined fucosylation profile. In one embodiment, the recombinant glycoprotein of interest comprises a predetermined mannosylation profile. In one embodiment, the recombinant glycoprotein of interest comprises a predetermined sialylation profile. In one embodiment, the recombinant glycoprotein of interest comprises a predetermined % biantennary glycoproteins profile. In one embodiment, the recombinant glycoprotein of interest comprises a predetermined % biantennary glycoproteins profile. In one embodiment, the recombinant glycoprotein of interest comprises a predetermined % triantennary glycoproteins profile. In one embodiment, the recombinant glycoprotein of interest comprises a predetermined biantennary glycoprotein to triantennary glycoprotein ratio.

In one embodiment, the recombinant glycoprotein of interest comprising a predetermined glycosylation profile is an anti-α4-integrin antibody. In another embodiment, the recombinant glycoprotein of interest comprising a predetermined glycosylation profile is an interferon beta-1a polypeptide. In another embodiment, the recombinant glycoprotein of interest comprising a predetermined glycosylation profile is a rFVIIIFc polypeptide.

In another embodiment, the predetermined galactosylation profile of the anti-α4-integrin antibody comprises 10 to 35% galactosylation, 13 to 32% galactosylation, 15 to 32% galactosylation, 16 to 30% galactosylation, 18 to 28% galactosylation, 18 to 31% galactosylation, 20 to 27% galactosylation, or 20 to 24% galactosylation. In another embodiment, the predetermined galactosylation profile of the anti-α4-integrin antibody comprises 13 to 32% or 18 to 31% galactosylation. In another embodiment, the predetermined galactosylation profile of the anti-α4-integrin antibody comprises about 10, 11, 12, 13, 14, 15, 16, 17, 18, 19, 20, 21, 22, 23, 24, 25, 26, 27, 28, 29, 30, 31, 32, 33, 34, or 35% galactosylation. In another embodiment, the predetermined galactosylation profile of the anti-α4-integrin antibody comprises X % galactosylation.

In another embodiment, the predetermined sialylation profile of the anti-α4-integrin antibody comprises 0.1 to 5% sialylation, 0.5 to 4.5% sialylation, 0.7 to 3.6% sialylation, 1.0 to 3.0% sialylation, 1.0 to 2.2% sialylation, X or 1.5 to 2.0% sialylation. In another embodiment, the predetermined sialylation profile of the anti-α4-integrin antibody comprises 0.7 to 3.6% or 1.0 to 2.2% sialylation. In another embodiment, the predetermined sialylation profile of the anti-α4-integrin antibody comprises about 0.1, 0.2, 0.5, 0.7, 0.8, 0.9, 1.0, 1.2, 1.4, 1.6, 1.8, 2.0, 2.2, 2.4, 2.5, 2.6, 2.8, 3.0, 3.2, 3.4, 3.5, 3.6, 3.8, 4.0, 4.2, 4.4, 4.5, 4.8, or 5.0% sialylation. In another embodiment, the predetermined sialylation profile of the anti-α4-integrin antibody comprises 1.6% sialylation.

In another embodiment, the predetermined sialylation profile of interferon beta-1a polypeptide comprises 75 to 100% sialylation, 80 to 100% sialylation, 95 to 100% sialylation, 85 to 100% sialylation, 91 to 100% sialylation, 75 to 97% sialylation, 80 to 97% sialylation, 85 to 97%, 91 to 97% sialylation, or 95 to 97% sialylation. In another embodiment, the predetermined sialylation profile of interferon beta-1a polypeptide comprises 91 to 100% or 91 to 97% sialylation. In another embodiment, the predetermined sialylation profile of interferon beta-1a polypeptide comprises about 75, 80, 85, 90, 91, 92, 93, 94, 95, 96, 97, 98, 99, or 100% sialylation. In another embodiment, the predetermined sialylation profile of interferon beta-1a polypeptide comprises 95% sialylation.

In another embodiment, the predetermined % biantennary glycoproteins profile of the interferon beta-1a polypeptide comprises 50 to 100% biantennary glycoproteins, 50 to 90% biantennary glycoproteins, 50 to 85% biantennary glycoproteins, 50 to 80% biantennary glycoproteins, 50 to 75% biantennary glycoproteins, 50 to 60% biantennary glycoproteins, 55 to 85% biantennary glycoproteins, 66 to 73% biantennary glycoproteins, 55 to 80% biantennary glycoproteins, or 66 to 70% biantennary glycoproteins. In another embodiment, the predetermined % biantennary glycoproteins profile of the beta-1a polypeptide comprises 55 to 85% or 66 to 73% biantennary glycoproteins. In another embodiment, the predetermined % biantennary glycoproteins profile of the beta-1a polypeptide comprises about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90% biantennary glycoproteins. In another embodiment, the predetermined % biantennary glycoproteins profile of the anti-α4-integrin antibody comprises 70% biantennary glycoproteins.

In another embodiment, the predetermined % triantennary glycoproteins profile of interferon beta-1a polypeptide comprises 10 to 50% triantennary glycoproteins, 10 to 45% triantennary glycoproteins, 12 to 46% triantennary glycoproteins, 10 to 35% triantennary glycoproteins, 20 to 35% triantennary glycoproteins, 26 to 35% triantennary glycoproteins, 10 to 35% triantennary glycoproteins, or 26 to 50% triantennary glycoproteins. In another embodiment, the predetermined % triantennary glycoproteins profile of interferon beta-1a polypeptide comprises 12 to 46% or 26 to 35% triantennary glycoproteins. In another embodiment, the predetermined % triantennary glycoproteins profile of interferon beta-1a polypeptide comprises about 10, 11, 12, 13, 14, 15, 16, 17, 18, 19, 20, 21, 22, 23, 24, 25, 26, 27, 28, 29, 30, 31, 32, 33, 34, or 35% triantennary glycoproteins. In another embodiment, the predetermined % triantennary glycoproteins profile of interferon beta-1a polypeptide comprises X % triantennary glycoproteins.

In another embodiment, the predetermined glycoproteins profile of interferon beta-1a polypeptide comprises biantennary glycoprotein to triantennary glycoprotein ratio of about 1.5 to 5, 1.8 to 5, 1.8 to 4.6, 1.5 to 4, 1.5 to 3.5, 1.5 to 3, 1.5 to 2.5, 2.0 to 2.5, 2.0 to 3, 2.5 to 3.5, 2.5 to 4, 2.5 to 4.5, 2.5 to 5.0, 3.0 to 4.0, 3.0 to 5.0, 3.0 to 5.0, 3.5 to 4.0, or 3.5 to 5.0. In another embodiment, the predetermined glycoproteins profile of interferon beta-1a polypeptide comprises biantennary glycoprotein to triantennary glycoprotein ratio of about 1.8 to 4.6 or about 2.0 to 2.5. In another embodiment, the predetermined glycoproteins profile of interferon beta-1a polypeptide comprises biantennary glycoprotein to triantennary glycoprotein ratio of about 1.5, 1.8, 2.0, 2.1, 2.2, 2.3, 2.4, 2.5, 2.6, 2.7, 2.8, 2.9, 3.0, 3.5, 4.0, 4.5, or 5.0. In another embodiment, the predetermined glycoproteins profile of interferon beta-1a polypeptide comprises biantennary glycoprotein to triantennary glycoprotein ratio of about 2.3.

In another embodiment, the predetermined glycosylation profile of the rFVIIIFc comprises 15 to 32% G0+Man6, 10 to 40% G0+Man6, 16 to 29% G0+Man6, 20 to 30% G0+Man6, 25 to 30% G0+Man6, 17 to 27% G0+Man6, 25 to 40% G0+Man6, or 15 to 20% G0+Man6. In another embodiment, the predetermined G0+Man6 profile of the rFVIIIFc comprises 15 to 32%, 16 to 29, or 17 to 27% G0+Man6. In another embodiment, the predetermined glycosylation profile of the rFVIIIFc comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% G0+Man6.

In another embodiment, the predetermined glycosylation profile of the rFVIIIFc comprises 10 to 40% G0+Man6, 19 to 30% G1+Man7, 15 to 40% G1+Man7, 20 to 40% G1+Man7, 25 to 40% G1+Man7, 30 to 40% G1+Man7, 10 to 30% G1+Man7, 20 to 30% G1+Man7, 22 to 27% G1+Man7, or 24 to 26% G1+Man7. In another embodiment, the predetermined G1+Man7 profile of the rFVIIIFc comprises 19 to 30, 22 to 27% or 24-26% G1+Man7. In another embodiment, the predetermined glycosylation profile of the rFVIIIFc comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40% G1+Man7.

In another embodiment, the predetermined glycosylation profile of the rFVIIIFc comprises 1 to 20% G2+Man9, 6 to 17% G2+Man9, 5 to 20% G2+Man9, 10 to 20% G2+Man9, 7 to 16% G2+Man9, 15 to 20% G2+Man9, 10 to 15% G2+Man9, or 5 to 15% G2+Man9. In another embodiment, the predetermined G2+Man9 profile of the rFVIIIFc comprises 6 to 17, 7 to 16% or 10-15% G2+Man9. In another embodiment, the predetermined glycosylation profile of the rFVIIIFc comprises about 1, 5, 6, 7, 8, 9, 10, 11, 12, 13, 14, 15, 16, 17, 18, 19, or 20% G2+Man9.

In one embodiment, the manganese concentration in the cell culture alters the levels of the isoform variants of the interferon beta-1a polypeptide. In one embodiment, the manganese concentration in the cell culture alters the level of an isoform of the interferon beta-1a polypeptide.

The present invention is applicable to altering, manipulating, or controlling the glycosylation pattern of a recombinant glycoprotein of interest to match, substantially match, approach, or more closely resemble the glycosylation pattern of the same glycoprotein, but produced in a different cell culture system. Recombinant glycoproteins of interest can be produced according to the invention using various different cell culture systems, e.g., a batch culture, fed-batch culture a perfusion culture, a shake flask, and/or a bioreactor. In one embodiment, cells expressing a recombinant glycoprotein of interest are cultured in basal medium to which the additive is introduced as a bolus, or two or more boli, from a stock solution. In another embodiment, the additive is introduced as a component of a feed medium. In certain embodiments the cell culture comprises a growth phase and a protein production phase, and the additive is introduced into the culture medium before, or at the same time as, or at some point after the initiation of the protein production phase.

In one embodiment, a medium described herein is a serum-free medium, animal protein-free medium or a chemically-defined medium. In a specific embodiment, a medium described herein is a chemically-defined medium.

In certain embodiments, the method comprises adding $MnCl_2$. $MnCl_2$ can be added to the culture medium in one bolus or two or more boli from a stock solution to, or be added as a component of a feed medium achieve a $MnCl_2$ concentration in the culture medium of between about 0.025 µM to about 10 µM $MnCl_2$ for anti-α4-integrin antibody. In certain embodiments the additive comprises $MnCl_2$, which can be added to the culture medium in one bolus or two or more boli from a stock solution, or be added as a component of a feed medium to achieve a $MnCl_2$ concentration in the culture medium between about 0.025 µM and about 10 µM, about 0.5 µM and about 10 µM, about 0.5 µM and about 7.5 µM, about 0.5 µM and about 5 µM, about 0.5 µM and about 2.5 µM, about 0.5 µM and about 1 µM, about 1 µM and about 10 µM, about 1 µM and about 10 µM, about 0.5 µM and about 7.5 µM, about 1 µM and about 5 µM, about 0.1 µM and about 2.5 µM, about 0.2 µM and about 2.5 µM, about 0.5 µM and about 2.5 µM, about 1 µM and about 2.5 µM, about 0.2 µM and about 2.0 µM, about 0.2 µM and about 1.5 µM, about 2.5 µM and about 10 µM, about 2.5 µM and about 7.5 µM, about 2.5 µM and about 5 µM, about 5 µM and about 10 µM, about 5 µM and about 7.5 µM or about 7.5 µM and about 10 µM for anti-α4-integrin antibody.

In another embodiment, the target manganese concentration in the culture medium is between 0.002 µM and 0.4 µM at Day 0 for anti-α4-integrin antibody. In another embodiment, the target manganese concentration in the culture mediums is between 0.04 µM and 1 at Day 13 for anti-α4-integrin antibody. In another embodiment, the manganese concentration is constantly monitored and maintained within the target manganese concentration range. In another embodiment, the target concentration is maintained through a feedback loop.

In certain embodiments, the method comprises adding $MnCl_2$. $MnCl_2$ can be added to the culture medium in one bolus or two or more boli from a stock solution to, or be added as a component of a feed medium achieve a $MnCl_2$ concentration in the culture medium of between about 0.1 µM to about 5 µM $MnCl_2$ for interferon beta-1a polypeptide. In certain embodiments the additive comprises $MnCl_2$, which can be added to the culture medium in one bolus or two or more boli from a stock solution, or be added as a component of a feed medium to achieve a $MnCl_2$ concentration in the culture medium between about 0.1 µM and about 5 µM, about 0.1 µM and about 4 µM, about 0.1 µM and about 3.5 µM, about 0.1 µM and about 3.0 µM, about 0.1 µM and about 2.5 µM, about 0.1 µM and about 2.0 µM, about 0.1 µM and about 1.5 µM, about 0.1 µM and about 1 µM, about 0.1 µM and about 0.5 µM, 0.2 µM and about 5 µM, about 0.2 µM and about 4 µM, about 0.2 µM and about 3.5 µM, about 0.2 µM and about 3.0 µM, about 0.2 µM and about 2.5 µM, about 0.2 µM and about 2.0 µM, about 0.2 µM and about 1.5 µM, about 0.2 µM and about 1 µM, about 0.2 µM and about 0.5 µM, 0.3 µM and about 5 µM, about 0.3 µM and about 4 µM, about 0.3 µM and about 3.5 µM, about 0.3 µM and about 3.0 µM, about 0.3 µM and about 2.5 µM, about 0.3 µM and about 2.0 µM, about 0.3 µM and about 1.5 µM, about 0.3 µM and about 1 µM, about 0.3 µM and about 0.5 µM about 0.5 µM and about 5 µM, about 0.5 µM and about 4 µM, about 0.5 µM and about 3 µM, about 0.5 µM and about 2.5 µM, about 0.5 µM and about 2.0 µM, about 0.5 µM and about 1.5 µM, about 0.5 µM and about 1 µM, about 1 µM and about 5 µM, about 1 µM and about 4 µM about, about 1 µM and about 3 µM, 1 µM and about 2.5 µM, about 2.5 µM and about 5 µM, about 0.2 µM to about 4.8 µM, or 0.3 µM to about 4.8 µM for interferon beta-1a polypeptide.

In certain embodiments, the method comprises adding $MnCl_2$. $MnCl_2$ can be added to the culture medium in one bolus or two or more boli from a stock solution to, or be added as a component of a feed medium achieve a $MnCl_2$ concentration in the culture medium of between about 30 nM to 1800 nM $MnCl_2$ for rFVIIIFc. In certain embodiments the additive comprises $MnCl_2$, which can be added to the culture medium in one bolus or two or more boli from a stock solution, or be added as a component of a feed medium to achieve a $MnCl_2$ concentration in the culture medium between about 25 nM to 1800 nM, 25 nM to 1500 nM, 30 nM to 1800 nM, 30 nM to 1500 nM, about 30 nM to 1000 nM, about 30 nM to 800 nM, about 30 nM to 500 nM, about 30 nM to 300 nM, 30 nM to 200 nM, about 30 nM to 100 nM, 50 nM to 1500 nM, about 50 nM to 1000 nM, about 50 nM to 800 nM, about 50 nM to 500 nM, about 50 nM to 300 nM, 50 nM to 200 nM, about 50 nM to 100 nM, 75 nM to 1500 nM, about 75 nM to 1000 nM, about 75 nM to 800 nM, about 75 nM to 500 nM, about 75 nM to 300 nM, 75 nM to 200 nM, about or 75 nM to 100 nM for rFVIIIFc.

In another embodiment, the manganese concentration is constantly monitored and maintained within the target manganese concentration range. In another embodiment, the target concentration is maintained through a feedback loop.

III. Cell Culture Compositions

The present invention further provides a cell culture composition comprising a medium described herein and cells, produced by the methods provided herein.

In one embodiment, a cell culture composition produced by the provided methods can be a batch culture, fed-batch culture or a perfusion culture. In a specific embodiment, a cell culture composition of the invention is a fed batch culture.

In one embodiment, a cell culture composition produced by the provided methods comprises eukaryotic cells. In another embodiment, a cell culture composition produced by the provided methods comprises mammalian cells selected from the group consisting of CHO cells, HEK cells, NS0 cells, PER.C6 cells, 293 cells, HeLa cells, and MDCK cells. In a specific embodiment, a cell culture composition described herein comprises CHO cells. In another specific embodiment, a cell culture composition described herein comprises HEK cells. In another specific embodiment, a cell culture composition described herein comprises hybridoma cells.

A cell culture composition produced by the provided methods can comprise cells that have been adapted to grow in serum free medium, animal protein free medium or chemically defined medium. Or it can comprise cells that have been genetically modified to increase their life-span in culture. In one embodiment, the cells have been modified to express an anti-α4-integrin antibody. In a further embodiment, the cells have been modified to express natalizumab.

The present invention provides a method of culturing cells, comprising contacting the cells with a medium disclosed herein, supplementing the medium as described above, or culturing cells in a medium supplemented as described above.

Cell cultures can be cultured in a batch culture, fed batch culture or a perfusion culture. In one embodiment, a cell culture according to a method of the present invention is a batch culture. In another embodiment, a cell culture according to a method of the present invention is a fed batch culture. In a further embodiment, a cell culture according to a method of the present invention is a perfusion culture. In certain embodiments the cell culture is maintained in a shake flask, in certain embodiments the cell culture is maintained in a bioreactor.

In one embodiment, a cell culture according to a method of the present invention is a serum-free culture. In another embodiment, a cell culture according to a method of the present invention is a chemically defined culture. In a further embodiment, a cell culture according to a method of the present invention is an animal protein free culture.

In one embodiment, a cell culture produced by the provided methods is contacted with a medium described herein during the growth phase of the culture. In another embodiment, a cell culture is contacted with a medium described herein during the production phase of the culture.

In one embodiment, a cell culture produced by the provided methods is contacted with a feed medium described herein during the production phase of the culture. In one embodiment, the culture is supplemented with the feed medium between about 1 and about 25 times during the second time period. In another embodiment, a culture is supplemented with the feed medium between about 1 and about 20 times, between about 1 and about 15 times, or between about 1 and about 10 times during the first time period. In a further embodiment, a culture is supplemented with the feed medium at least once, at least twice, at least three times, at least four times, at least five times, at least 6 times, at least 7 times, at least 8 times, at least 9 times, at least 10 times, at least 11 times, at least 12 times, at least 13 times, at least 14 times, at least 15 times, at least 20 times, at least 25 times. In a specific embodiment, the culture is a fed batch culture. In another specific embodiment, the culture is a perfusion culture.

A culture produced by the provided methods can be contacted with a feed medium described herein at regular intervals. In one embodiment, the regular interval is about once a day, about once every two days, about once every three days, about once every 4 days, or about once every 5 days. In a specific embodiment, the culture is a fed batch culture. In another specific embodiment, the culture is a perfusion culture.

A culture produced by the provided methods can be contacted with a feed medium described herein on an as needed basis based on the metabolic status of the culture. In one embodiment, a metabolic marker of a fed batch culture is measured prior to supplementing the culture with a feed medium described herein. In one embodiment, the metabolic marker is selected from the group consisting of: glucose concentration, lactate concentration, ammonium concentration, alanine concentration, glutamine concentration, glutamate concentration, cell specific lactate production rate to the cell specific glucose uptake rate ratio (LPR/GUR ratio), and Rhodamine 123 specific cell fluorescence. In one embodiment, an LPR/GUR value of >0.1 indicates the need to supplement the culture with a feed medium described herein. In a further specific embodiment, a lactate concentration of >3 g/L indicates the need to supplement the culture with a feed medium described herein. In another embodiment, a culture according to the present invention is supplemented with a feed medium described herein when the LPR/GUR value of the culture is >0.1 or when the lactate concentration of the culture is >3 g/L. In a specific embodiment, the culture is a fed batch culture. In another specific embodiment, the culture is a perfusion culture.

In one embodiment, a medium described herein is a feed medium for a fed batch cell culture. A skilled artisan understands that a fed batch cell culture can be contacted with a feed medium more than once. In one embodiment, a fed batch cell culture is contacted with a medium described herein only once. In another embodiment, a fed batch cell culture is contacted with a medium described herein more than once, for example, at least twice, at least three times, at least four times, at least five times, at least six times, at least seven times, or at least ten times.

In accordance with the present invention, the total volume of feed medium added to a cell culture should optimally be kept to a minimal amount. For example, the total volume of the feed medium added to the cell culture can be 1, 2, 3, 4, 5, 6, 7, 8, 9, 10, 15, 20, 25, 30, 35, 40, 45 or 50% of the volume of the cell culture prior to adding the feed medium.

Cell cultures produced by the provided methods can be grown to achieve a particular cell density, depending on the needs of the practitioner and the requirement of the cells themselves, prior to being contacted with a medium described herein. In one embodiment, the cell culture is contacted with a medium described herein at a viable cell density of 1, 5, 10, 15, 20, 25, 30, 35, 40, 45, 50, 55, 60, 65, 70, 75, 80, 85, 90, 95 or 99 percent of maximal viable cell density. In a specific embodiment, the medium is a feed medium.

Cell cultures produced by the provided methods can be allowed to grow for a defined period of time before they are contacted with a medium described herein. In one embodiment, the cell culture is contacted with a medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the cell culture. In another embodiment, the cell culture is contacted with a medium described herein at week 1, 2, 3, 4, 5, 6, 7, or 8 of the cell culture. In a specific embodiment, the medium is a feed medium.

Cell cultures produced by the provided methods can be cultured in the production phase for a defined period of time. In one embodiment, the cell culture is contacted with a feed medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the production phase.

A culture produced by the provided methods can be maintained in production phase for between about 1 day and about 30 days. In one embodiment, a culture is maintained in production phase for between about 1 day and about 30 days, between about 1 day and about 25 days, between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 25 days, about 3 days and about 25 days, about 4 days and about 25 days, about 5 days and about 25 days, about 6 days and about 25 days, about 7 days and about 25 days, about 8 days and about 25 days, about 9 days and about 25 days, about 10 days and about 25 days, about 15 days and about 25 days, about 20 days and about 25 days, about 2 days and about 30 days, about 3 days and about 30 days, about 4 days and about 30 days, about 5 days and about 30 days, about 6 days and about 30 days, about 7 days and about 30 days, about 8 days and about 30 days, about 9 days and about 30 days, about 10 days and about 30 days, about 15 days and about 30 days, about 20 days and about 30 days, or about 25 days and about 30 days. In another embodiment, a culture is maintained in production phase for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, at least about 20 days, at least about 25 days, or at least about 30 days. In a further embodiment, a culture is maintained in production phase for about 1 day, about 2 days, about 3 days, about 4 days, about 5 days, about 6 days, about 7 days, about 8 days, about 9 days, about 10 days, about 11 days, about 12 days, about 15 days, about 20 days, about 25 days, or about 30 days.

The present invention further provides a method of producing a recombinant glycoprotein interest, comprising culturing cells engineered to express the recombinant glycoprotein of interest in a culture comprising a medium described herein; and recovering or isolating the recombinant glycoprotein of interest from the culture. In certain embodiments, the recombinant glycoprotein of interest is an antibody or a fragment thereof. In a specific embodiment, the recombinant glycoprotein of interest is an anti-α4-integrin antibody. In another embodiment, the recombinant glycoprotein of interest is natalizumab.

In a specific embodiment, a method of producing a recombinant glycoprotein of interest according to the present invention produces a maximum glycoprotein titer of at least about 0.05 g/L, at least about 0.1 g/L, at least about 0.25 g/L, at least about 0.5 g/L, at least about 0.75 g/L, at least about 1.0 g/L, at least about 1.5 g/L, at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter. In another embodiment, the method according to the present invention produces a maximum glycoprotein titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In a specific embodiment, the glycoprotein is an antibody. In another embodiment, the glycoprotein is a blood clotting factor.

The invention further provides a conditioned cell culture medium produced by a method described herein.

In one embodiment, a conditioned cell culture medium produced according to the provided methods comprises a recombinant glycoprotein of interest. In a specific embodiment, a conditioned cell culture medium according to the invention comprises a recombinant glycoprotein of interest at a titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter, or a titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In another embodiment, a conditioned cell culture medium according to the invention comprises a recombinant glycoprotein at a higher titer than the titer obtained without the use of a medium described herein. In a specific embodiment, the protein or polypeptide is an antibody.

Anti-α4-Integrin Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any anti-α4-integrin antibody that can be expressed in a host cell can be used in accordance with the present invention. In one embodiment, the anti-α4-integrin antibody to be expressed is a monoclonal antibody.

Particular anti-α4-integrin antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667, 988; and 5,885,793.

In addition to the use of display libraries, other methods can be used to obtain an antibody. For example, a protein or a peptide thereof can be used as an antigen in a non-human animal, e.g., a rodent, i.e., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity can be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal anti-α4-integrin antibody is obtained from the non-human animal, and then modified, e.g., humanized or deimmunized. Winter describes an exemplary CDR-grafting method that can be used to prepare humanized antibodies described herein (U.S. Pat. No. 5,225,539). All or some of the CDRs of a particular human antibody can be replaced with at least a portion of a non-human antibody. In one embodiment, it is only necessary to replace the CDRs required for binding or binding determinants of such CDRs to arrive at a useful humanized antibody that binds to an antigen.

Humanized anti-α4-integrin antibodies can be generated by replacing sequences of the Fv variable region that are not directly involved in antigen binding with equivalent sequences from human Fv variable regions. General methods for generating humanized antibodies are provided by Morrison, S. L. (1985) *Science* 229:1202-1207, by Oi et al. (1986) *BioTechniques* 4:214, and by U.S. Pat. Nos. 5,585, 089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector. In one embodiment, the expression vector comprises a polynucleotide encoding a glutamine synthetase polypeptide. (See, e.g., Porter et al., *Biotechnol Prog* 26(5):1446-54 (2010).). In one embodiment, humanized anti-α4-integrin antibody is natalizumab.

The anti-α4-integrin antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies can have mutations in the CH2 region of the heavy chain that reduce or alter effector function, e.g., Fc receptor binding and complement activation. For example, antibodies can have mutations such as those described in U.S. Pat. Nos. 5,624, 821 and 5,648,260. Antibodies can also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

In other embodiments, the anti-α4-integrin antibody can be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies can be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.* 22:259-306. Removal of any carbohydrate moieties present on the antibodies can be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138:350). See, e.g., U.S. Pat. No. 5,869,046 for a modification that increases in vivo half-life by providing a salvage receptor binding epitope.

The anti-α4-integrin antibodies can be in the form of full length antibodies, or in the form of fragments of antibodies, e.g., Fab, F(ab')₂, Fd, dAb, and scFv fragments. Additional forms include a protein that includes a single variable domain, e.g., a camel or camelized domain. See, e.g., U.S. 2005-0079574 and Davies et al. (1996) *Protein Eng.* 9(6): 531-7.

In one embodiment, the anti-α4-integrin antibody is an antigen-binding fragment of a full length antibody, e.g., a Fab, F(ab')2, Fv or a single chain Fv fragment. Typically, the anti-α4-integrin antibody is a full length antibody. The anti-α4-integrin antibody can be a monoclonal antibody or a mono-specific antibody.

In another embodiment, the anti-α4-integrin antibody can be a human, humanized, CDR-grafted, chimeric, mutated, affinity matured, deimmunized, synthetic or otherwise in vitro-generated antibody, and combinations thereof.

The heavy and light chains of the anti-α4-integrin antibody can be substantially full-length. The protein can include at least one, and preferably two, complete heavy chains, and at least one, and preferably two, complete light chains or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

Interferon Beta-1a Polypeptide

Interferons are a family of naturally-occurring, relatively small, single-chain glycoproteins that are produced by eukaryotic cells in response to viral infection and other biological inducers. Interferons are grouped into three major classes, designated: 1) leukocyte interferon (interferon-alpha), 2) fibroblast interferon (interferon-beta), and 3) immune interferon (interferon-gamma). In response to viral infection, lymphocytes primarily synthesize interferon-alpha (with interferon-gamma), whereas fibroblasts usually synthesize interferon-beta. There are two types of Interferon-beta: Interferon beta-1 and Interferon beta-3.

In one embodiment, Interferon beta is a mammalian, human, mouse, humanized or chimeric Interferon beta. In another embodiment, Interferon beta is a recombinant Interferon beta.

In one embodiment, Interferon beta is Interferon beta-1. In another embodiment, Interferon beta-1 is Interferon beta-1a (or Interferon beta-1a polypeptide). In one embodiment, Interferon beta-1a is mammalian, human, mouse, humanized, or chimeric Interferon beta-1a. In another embodiment, Interferon beta-1a is a recombinant Interferon beta-1a.

In one embodiment, Interferon beta-1a is a fragment of full length, naturally-occurring Interferon beta-1a. In another embodiment, Interferon beta-1a is modified or mutated Interferon beta-1a. In another embodiment, Interferon beta-1a is a variant of the naturally-occurring Interferon beta-1a. In one embodiment, Interferon beta-1a is a glycosylation variant.

Interferons with modified activity have been generated (for example, U.S. Pat. Nos. 6,514,729; 4,738,844; 4,738,845; 4,753,795, which are incorporated by reference herein). U.S. Pat. Nos. 5,545,723 and 6,127,332, which are incorporated by reference herein in its entirety, disclose mutant interferon beta. Chimeric interferons comprising sequences from one or more interferons have been made (for example, Chang et al., Nature Biotech. 17(8):793-797 (1999), U.S. Pat. Nos. 4,758,428; 5,738,846, which are incorporated by reference in their entirety). Substitution mutants of interferon beta at positions 49 and 51 have also been described (for example, U.S. Pat. No. 6,531,122, which is incorporated by reference in its entirety). Expression and generation of IFN beta variants (such as glycosylation variants) and conjugates have been discussed, for example, in U.S. Pat. No. 7,144,574, which is incorporated by reference herein in its entirety.

Interferon-beta variants with enhanced stability have been discussed, in which the hydrophobic core was optimized using rational design methods (for example, WO 00/68387, which is incorporated by reference in its entirety). Alternate formulations that promote interferon stability or solubility have also been disclosed (for example, U.S. Pat. Nos. 4,675,483; 5,730,969; 5,766,582; WO 02/38170, which are incorporated by reference in their entirety).

Interferon-beta mutants with enhanced solubility have been discussed, in which several leucine and phenylalanine residues are replaced with serine, threonine, or tyrosine residues (for example, WO 98/48018, which is incorporated by reference in its entirety). Other modifications to improve solubility are discussed, for example, in US 2005/0054053 which is incorporated by reference herein in its entirety. Interferon-beta variants with reduced immunogenicity have been discussed (for example, WO 02/074783, which is incorporated by reference in its entirety).

In one embodiment, the interferon beta-1a polypeptide is AVONEX®. AVONEX® is a 166 amino acid recombinant glycoprotein produced by Chinese Hamster Ovary cells and has a molecular weight of approximately 22,500 Daltons and amino acid sequence of SEQ ID NO:1.

In one embodiment, the Interferon beta-1a polypeptide is a fragment of AVONEX®. In another embodiment, Interferon beta-1a is a polypeptide having 99%, 98%, 97%, 96%, 95%, 94%, 93%, 92%, 91%, 90%, 89%, 88%, 87%, 86%, 85%, 84%, 83%, 82%, 81%, or 80% homology with AVONEX®. In one embodiment, the Interferon beta-1a polypeptide is a variant or mutant of AVONEX®.

Factor VIII Polypeptide

The Factor VIII polypeptide as used herein is functional factor VIII polypeptide in its normal role in coagulation, unless otherwise specified. Thus, the term Factor VIII includes variant polypeptides that are functional. Factor VIII proteins can be the human, porcine, canine, and murine factor VIII proteins. The full length polypeptide and polynucleotide sequences are known, as are many functional fragments, mutants and modified versions. Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., *Hum. Mutat.* 19:274-8 (2002)), incorporated herein by reference in its entirety. In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human factor VIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

The porcine factor VIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of factor VIII sequences from a pig spleen cDNA library has been reported (Healey, J. F. et al., Blood 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

In one embodiment, Factor VIII is a recombinant protein comprising human coagulation Factor VIII (FVIII) covalently linked to the Fc domain of human immunoglobulin G1 (IgG1) (rFVIIIFc). See, e.g., Peters et al., J. of Thrombosis & Haemostasis, 11:132-141 (2012); McCue et al., J Chromatogr A., 1216(45):7824-7830 (2009); US 2014/0370035 A1; US 2013/0108629, all incorporated herein by reference in their entirety.

In one embodiment, rFVIIIFc was be obtained by transfecting expression vector into human embryonic kidney 293 cells (HEK293H; Invitrogen) using Lipofectamine 2000 transfection reagent (Invitrogen) at Biogen (Cambridge, Mass.). A stable clonal cell lines were generated by selection with Zeocin (Invitrogen) to produce FVIIIFc. See McCue et al., J Chromatogr A. 1216(45):7824-7830 (2009)).

Cells

Any eukaryotic cell or cell type susceptible to cell culture can be utilized in accordance with the present invention. For example, plant cells, yeast cells, animal cells, insect cells, avian cells or mammalian cells can be utilized in accordance with the present invention. In one embodiment, the eukaryotic cells are capable of expressing a recombinant protein or are capable of producing a recombinant or reassortant virus.

Non-limiting examples of mammalian cells that can be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells ±DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TM cells (Mather et al., Annals N.Y. Acad. Sci., 383:44-68 (1982)); MRC 5 cells; FS4 cells; and a human hepatoma line (Hep G2). In one embodiment, the present invention is used in the culturing of and expression of polypeptides from CHO cell lines. In a specific embodiment, the CHO cell line is the DG44 CHO cell line. In a specific embodiment, the CHO cell line is the DUXB11 CHO cell line. In a specific embodiment, the CHO cell line comprises a vector comprising a polynucleotide encoding a glutamine synthetase polypeptide. In a further specific embodiment, the CHO cell line expresses an exogenous glutamine synthetase gene. (See, e.g., Porter et al., Biotechnol Prog 26(5):1446-54 (2010).). In one embodiment, the present invention is used in the culturing of and expression of polypeptides from HEK cell lines.

Additionally, any number of commercially and non-commercially available hybridoma cell lines that express polypeptides or proteins can be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

The eukaryotic cells according to the present invention can be selected or engineered to produce high levels of protein or polypeptide, or to produce large quantities of virus. Often, cells are genetically engineered to produce high levels of protein, for example by introduction of a gene encoding the recombinant glycoprotein of interest and/or by introduction of control elements that regulate expression of the gene (whether endogenous or introduced) encoding the recombinant glycoprotein of interest.

The eukaryotic cells can also be selected or engineered to survive in culture for extended periods of time. For example, the cells can be genetically engineered to express a polypeptide or polypeptides that confer extended survival on the cells. In one embodiment, the eukaryotic cells comprise a transgene encoding the Bcl-2 polypeptide or a variant thereof. See, e.g., U.S. Pat. No. 7,785,880. In a specific embodiment, the cells comprise a polynucleotide encoding the bcl-xL polypeptide. See, e.g., Chiang G G, Sisk W P. 2005. *Biotechnology and Bioengineering* 91(7):779-792.

The eukaryotic cells can also be selected or engineered to modify its posttranslational modification pathways. In one embodiment, the cells are selected or engineered to modify a protein glycolsylation pathway. In a specific embodiment, the cells are selected or engineered to express an aglycosylated protein, e.g., an aglycosylated recombinant antibody. In another specific embodiment, the cells are selected or engineered to express an afucosylated protein, e.g., an afucosylated recombinant antibody.

The eukaryotic cells can also be selected or engineered to allow culturing in serum free medium.

Media

The cell culture of the present invention is prepared in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, manganese, selenium and tricarboxylic acid intermediates), hydrolysates (hydrolyzed proteins derived from plant or animal sources), and combinations thereof. Commercially available media such as 5x-concentrated DMEM/F12 (Invitrogen), CD OptiCHO feed (Invitrogen), CD EfficientFeed (Invitrogen), Cell Boost (HyClone), BalanCD CHO Feed (Irvine Scientific), BD Recharge (Becton Dickinson), Cellvento Feed (EMD Millipore), Ex-cell CHOZN Feed (Sigma-Aldrich), CHO Feed Bioreactor Supplement (Sigma-Aldrich), SheffCHO (Kerry), Zap-CHO (Invitria), ActiCHO (PAA/GE Healthcare), Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979) *Meth. Enz.,* 58:44; Barnes and Sato, (1980) *Anal. Biochem.,* 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. In some embodiments the nutrient media is serum-free media, a protein-free media, or a chemically defined media. Any other necessary supplements can also be included at appropriate concentrations that would be known to those skilled in the art.

In one embodiment, the mammalian host cell is a CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) with modified concentrations of some components such as amino acids, salts, sugar, and vitamins, recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements. In another embodiment, the suitable medium contains yeast hydrolysate. In a preferred embodiment, the suitable medium contains yeastolate.

The present invention provides a variety of media formulations that, when used in accordance with other culturing steps described herein, minimize or prevent decreases in cellular viability in the culture while retaining the ability to control glycosylation of a recombinant glycoprotein of interest.

A media formulation of the present invention that has been shown to be to useful in manipulating glycosylation, while not having greatly negative impacts on metabolic balance, cell growth and/or viability or on expression of polypeptide or protein comprises the media supplement described herein. One of ordinary skill in the art will understand that the media formulations of the present invention encompass both defined and non-defined media.

Cell Culture Processes

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities (seed density) can range from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

In accordance with the present invention, a cell culture size can be any volume that is appropriate for production of polypeptides. In one embodiment, the volume of the cell culture is at least 500 liters. In other embodiments, the volume of the production cell culture is 10, 50, 100, 250, 1000, 2000, 2500, 5000, 8000, 10,000, 12,000 liters or more, or any volume in between. For example, a cell culture will be 10 to 5,000 liters, 10 to 10,000 liters, 10 to 15,000 liters, 50 to 5,000 liters, 50 to 10,000 liters, or 50 to 15,000 liters, 100 to 5,000 liters, 100 to 10,000 liters, 100 to 15,000 liters, 500 to 5,000 liters, 500 to 10,000 liters, 500 to 15,000 liters, 1,000 to 5,000 liters, 1,000 to 10,000 liters, or 1,000 to 15,000 liters. Or a cell culture will be between about 500 liters and about 30,000 liters, about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a cell culture will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose a suitable culture size for use in practicing the present invention. The production bioreactor for the culture can be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In certain cases, it can be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively or additionally, it can be beneficial or necessary to supplement the cell culture prior to the subsequent production phase. As non-limiting examples, it can be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, can all be added to the cell culture at one time, or they can be provided to the cell culture in a series of additions. In one embodiment of the present invention, the supplementary components are provided to the cell culture at multiple times in proportional amounts. In another embodiment, it can be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture can be 1, 2, 3, 4, 5, 6, 7, 8, 9, 10, 15, 20, 25, 30, 35, 40, 45 or 50% of the volume of the cell culture prior to providing the supplementary components.

The cell culture can be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner can find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase.

In order to monitor certain cell culture conditions, it will be necessary to remove small aliquots of the culture for analysis. One of ordinary skill in the art will understand that such removal can potentially introduce contamination into the cell culture, and will take appropriate care to minimize the risk of such contamination.

As non-limiting example, it can be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density can be measured using a hemacytometer, a Coulter counter, or Cell density examination (CEDEX). Viable cell density can be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It can also be beneficial or necessary to monitor the posttranslational modifications of the expressed polypeptide or protein, including phosphorylation and glycosylation.

The practitioner can also monitor the metabolic status of the cell culture, for example, by monitoring the glucose, lactate, ammonium, and amino acid concentrations in the cell culture, as well as by monitoring the oxygen production or carbon dioxide production of the cell culture. For example, cell culture conditions can be analyzed by using NOVA Bioprofile 100 or 400 (NOVA Biomedical, Wash.). Additionally, the practitioner can monitor the metabolic state of the cell culture by monitoring the activity of mitochondria. In one embodiment, mitochondrial activity can be monitored by monitoring the mitochondrial membrane potential using Rhodamine 123. Johnson L V, Walsh M L, Chen L B. 1980. *Proceedings of the National Academy of Sciences* 77(2):990-994.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids can be removed, as by centrifugation or filtering for example, as a first step in the purification process.

Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein can be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide can be formulated as a pharmaceutical composition for administration to a subject, e.g., to treat or prevent a disorder or disease. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (See e.g., Berge, S. M., et al. (1977) *J. Pharm. Sci.* 66:1-19). In one embodiment, a pharmaceutical composition is an immunogenic composition comprising a virus produced in accordance with methods described herein.

Pharmaceutical formulation is a well-established art, and is further described, e.g., in Gennaro (ed.), Remington. The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

The pharmaceutical compositions can be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically compositions for the agents described herein are in the form of injectable or infusible solutions.

In one embodiment, the antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; Gene Transfer Vectors For Mammalian Cells, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical—Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* 4$^{th}$ ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, Genes VIII, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1: Interferon Beta-1a

Interferon beta-1a was produced in a cell culture under controlled conditions using a Chinese Hamster Ovary (CHO) cell line recombinantly producing interferon beta-1a. Cells expressing interferon beta-1a were expanded from a vial per standard techniques in shake flasks. To investigate the impact of manganese specifically, cells were split from the shake flasks into 5 L bioreactors containing medium with various levels of manganese supplementation. The only variable in cultivation conditions was the level of manganese supplemented to cell culture and all other medium components and cell culture process conditions were unchanged. The level of manganese ranged from 0-4800 nM (that is 4.8 µM) supplementation at inoculation on day 0. At harvest, glycosylation, specifically the level of biantennary, TriLac, and triantennary species, of interferon beta-1a was analyzed by LC/MS. Sialylation in the same experiment was assessed by a glycan method using 2-aminobenzoic acid labeling. The data shown in FIG. 1A and FIG. 1B demonstrates that at least 100 nM manganese, preferably 300 nM manganese, is required in order to produce consistent glycosylation.

Example 2. rFVIIIFc rFVIIIFc was produced in a cell culture under controlled conditions using a HEK293 cells recombinantly producing rFVIIIFc. Cells expressing rFVIIIFc were expanded from a vial per standard techniques in shake flasks. To investigate the impact of manganese specifically, cells were split from the shake flasks into 5 L bioreactors containing medium with various levels of manganese supplementation. The only variable in cultivation conditions was the level of manganese supplemented to cell culture and all other medium components and cell culture process conditions were unchanged. The level of manganese ranged from 0-1800 nM manganese (that is 1.8 μM) supplementation at inoculation on day 0. At harvest, glycosylation, specifically the level of level of G0+Man6, G1+Man7, and G2+Man9, of rFVIIIFc was analyzed by CELIF. Separately mannose species were characterized by LC/MS. There was no change in mannosylation (mannose species) level, so the changes in glycosylated species are all changes in galactosylation level. The data shown in FIG. 2 demonstrates that at least 50 nM manganese is required to produce consistent galactosylation.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method for achieving a predetermined glycosylation profile of an anti-α4-integrin antibody, an interferon beta-1a polypeptide, or a rFVIIIFc, the method comprising:
    adding manganese to a cell culture at a concentration that falls within a target manganese concentration range, wherein the cell culture comprises host cells producing the anti-α4-integrin antibody, interferon beta-1a polypeptide, or rFVIIIFc, and if the manganese concentration in the cell culture is below the target manganese concentration range, the cell culture is supplemented with manganese, wherein the target manganese concentration range in the cell culture for an anti-α4-integrin antibody, an interferon beta-1a polypeptide, or a rFVIIIFc is respectively 0.025 μM to 10 μM, 0.1 μM to 5 μM, and 30 nM to 1800 nM.

2. A method for achieving a predetermined glycosylation profile of an anti-α4-integrin antibody, an interferon beta-1a polypeptide, or a rFVIIIFc, the method comprising (i) determining a manganese concentration in an ingredient or an additive of a cell culture medium, (ii) if the manganese concentration is below a target manganese concentration range, adding manganese to the ingredient or the additive of the cell culture medium and supplementing the cell culture medium with the ingredient or the additive to achieve a manganese concentration within the target manganese concentration range, (iii) producing a cell culture medium with the target manganese concentration comprising the ingredient or the additive of the cell culture medium, and (iv) culturing a recombinant host cell producing an anti-α4-integrin antibody, an interferon beta-1a polypeptide, or a rFVIIIFc in the cell culture medium; wherein the target manganese concentration range in the cell culture for an anti-α4-integrin antibody, an interferon beta-1a polypeptide, or a rFVIIIFc is respectively 0.025 µM to 10 µM, 0.1 µM to 5 µM, and 30 nM to 1800 nM.

3. The method of claim 1, wherein the predetermined glycosylation profile of the anti-α4-integrin antibody comprises 13 to 32%, 18 to 31%, or about 24% galactosylation.

4. The method of claim 1, wherein the predetermined glycosylation profile of the anti-α4-integrin antibody comprises 0.7 to 3.6%, 1.0 to 2.2%, or about 1.6% sialylation.

5. The method of claim 1, wherein the host cells produce anti-α4-integrin antibody and the target manganese concentration range in the cell culture is 0.1 µM to 2.5 µM, or 0.2 µM to 2 µM.

6. The method of claim 1, wherein the target manganese concentration range in the cell culture is at day 0 between 0.025 µM and 0.4 µM and at day 13 between 0.04 µM and 1 µM.

7. The method of claim 1, wherein the manganese concentration alters levels of isoform variants of the anti-α4-integrin antibody or of the interferon beta-1a polypeptide.

8. The method of claim 7, wherein the anti-α4-integrin antibody is natalizumab.

9. The method of claim 1, wherein the predetermined glycosylation profile of the interferon beta-1a polypeptide comprises 91 to 100%, 91 to 97%, or 95% sialylation.

10. The method of claim 1, wherein the predetermined glycosylation profile of the interferon beta-1a polypeptide comprises 55 to 85%, 66 to 73%, or 70% biantennary glycoproteins.

11. The method of claim 1, wherein the predetermined glycosylation profile of the interferon beta-1a polypeptide comprises 12 to 46%, 26 to 35%, or 30% triantennary glycoproteins.

12. The method of claim 1, wherein the predetermined glycosylation profile of the interferon beta-1a polypeptide comprises a biantennary glycoprotein to triantennary glycoprotein ratio of about 1.8 to 4.6, about 2.0 to 2.5, or about 2.3.

13. The method of claim 1, wherein the host cells produce interferon beta-1a polypeptide and the target manganese concentration range in the cell culture is 0.2 µM to 4.8 µM, or 0.3 µM to 4.8 µM.

14. The method of claim 1, wherein the interferon beta-1a polypeptide has the sequence of SEQ ID NO:1.

15. The method of claim 1, wherein the predetermined glycosylation profile of the rFVIIIFc comprises 15 to 32% G0+Man6, 16 to 29% G0+Man6, or 17 to 27% G0+Man6.

16. The method of claim 1, wherein the predetermined glycosylation profile of the rFVIIIFc comprises 19 to 30% G1+Man7, 22 to 27% G1+Man7, or 24 to 26% G1+Man7.

17. The method of claim 1, wherein the predetermined glycosylation profile of the rFVIIIFc comprises 6 to 17% G2+Man9, 7 to 16% G2+Man9, or 10 to 15% G2+Man9.

18. The method of claim 1, wherein the host cells produce rFVIIIFc and the target manganese concentration range in the cell culture is 50 nM to 300 nM, or 75 nM to 200 nM.

19. The method of claim 1, wherein the target manganese concentration is maintained through a feedback loop, optionally wherein the manganese concentration is constantly monitored and maintained within the target manganese concentration range, and optionally wherein the target manganese concentration is achieved with a single dose of manganese.

20. The method of claim 1, wherein the anti-α4-integrin antibody, the interferon beta-1a polypeptide, or the rFVIIIFc are produced by a eukaryotic host cell, optionally wherein the eukaryotic host cell is a mammalian host cell, and optionally wherein the anti-α4-integrin antibody, interferon beta-1a polypeptide, or rFVIIIFc are produced at a manufacturing scale.

21. The method of claim 1, wherein the manganese concentration in the cell culture falls below the target manganese concentration when the host cells produce the anti-α4-integrin antibody, interferon beta-1a polypeptide, or rFVIIIFc, and the cell culture is supplemented with manganese.

* * * * *